(12) United States Patent
Barry et al.

(10) Patent No.: US 6,582,715 B1
(45) Date of Patent: *Jun. 24, 2003

(54) ANTIMICROBIAL ORTHOPEDIC IMPLANTS

(75) Inventors: John E. Barry, Derry, NH (US); Jeffrey A. Trogolo, Boston, MA (US)

(73) Assignee: AgION Technologies, Inc., Wakefield, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/300,687

(22) Filed: Apr. 27, 1999

(51) Int. Cl.$^7$ .............................. A61F 13/00; A61F 2/00
(52) U.S. Cl. ..................... 424/422; 424/423; 424/425; 623/23.56; 623/23.57; 623/23.58; 623/23.59; 623/23.6; 623/23.61; 623/23.52; 623/23.53; 623/16.11; 623/17.17; 623/17.18; 623/17.19
(58) Field of Search ..................... 424/79, 443; 623/11; 427/376.2; 428/323

(56) References Cited

U.S. PATENT DOCUMENTS

| | | | |
|---|---|---|---|
| 4,612,337 A | | 9/1986 | Fox, Jr. et al. ............. 523/113 |
| 4,615,705 A | * | 10/1986 | Scales et al. ................. 623/11 |
| 4,775,585 A | * | 10/1988 | Hagiwara ................... 428/323 |
| 4,911,899 A | | 3/1990 | Hagiwara et al. ........... 423/118 |
| 4,923,450 A | | 5/1990 | Meada et al. ............... 604/265 |
| 4,938,955 A | * | 7/1990 | Niira et al. .................... 424/79 |
| 4,938,958 A | | 7/1990 | Niira et al. .................... 424/79 |
| 5,100,671 A | * | 3/1992 | Maeda et al. ............... 424/443 |
| 5,151,122 A | * | 9/1992 | Atsumi et al. |
| 5,180,585 A | | 1/1993 | Jacobson et al. ........... 424/405 |
| 5,296,238 A | | 3/1994 | Sugiura et al. ............. 424/604 |
| 5,474,797 A | | 12/1995 | Sioshansi et al. .......... 427/2.24 |
| 5,478,563 A | | 12/1995 | Erami ........................ 424/409 |
| 5,492,763 A | | 2/1996 | Barry et al. ................ 428/457 |
| 5,556,699 A | | 9/1996 | Niira et al. .................. 428/323 |
| 5,607,464 A | | 3/1997 | Trescony et al. .............. 623/1 |
| 5,609,629 A | | 3/1997 | Fearnot et al. ................ 623/1 |
| 5,614,568 A | | 3/1997 | Mawatari et al. ........... 523/122 |
| 5,647,858 A | | 7/1997 | Davidson .................... 604/264 |
| 5,688,561 A | * | 11/1997 | Ichikawa et al. ........ 427/376.6 |
| 5,709,870 A | | 1/1998 | Yoshimura et al. ......... 424/405 |
| 5,731,087 A | | 3/1998 | Fan et al. .................... 428/412 |
| 5,753,251 A | | 5/1998 | Burrell et al. .............. 424/426 |
| 5,756,145 A | | 5/1998 | Darouiche ................. 427/2.24 |
| 5,770,255 A | | 6/1998 | Burrell et al. ............... 427/2.1 |
| 5,783,570 A | | 7/1998 | Yokota et al. ................ 514/56 |
| 6,015,816 A | * | 1/2000 | Kostyniak et al. |

* cited by examiner

Primary Examiner—Thurman K. Page
Assistant Examiner—Isis Ghali
(74) Attorney, Agent, or Firm—Edward K. Welch, II

(57) ABSTRACT

An orthopedic surgical implant of one or more components having a surface which is to be contacted by body tissue and/or fluid. The surface contains an inorganic antimicrobial agent either incorporated in the material forming a component having the surface or incorporated in a coating, such as of the adhesive or powder spray type, applied to the surface.

25 Claims, 1 Drawing Sheet

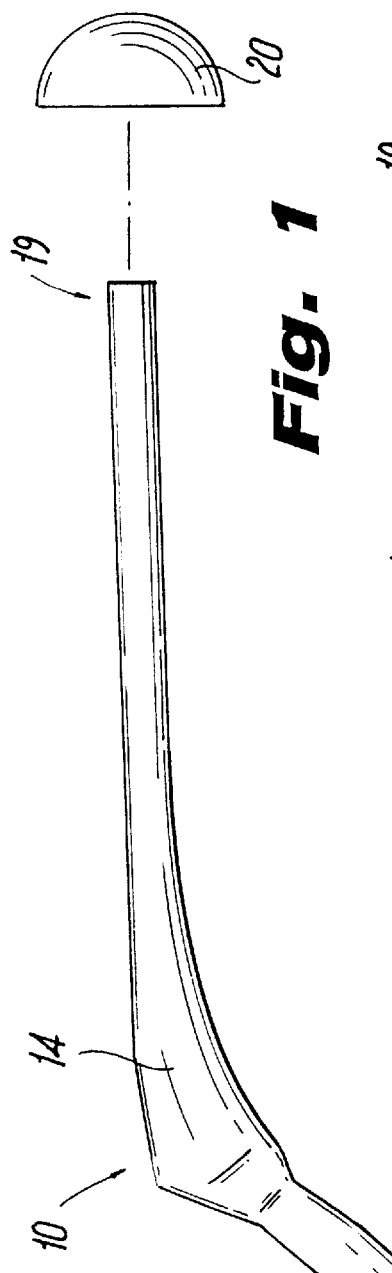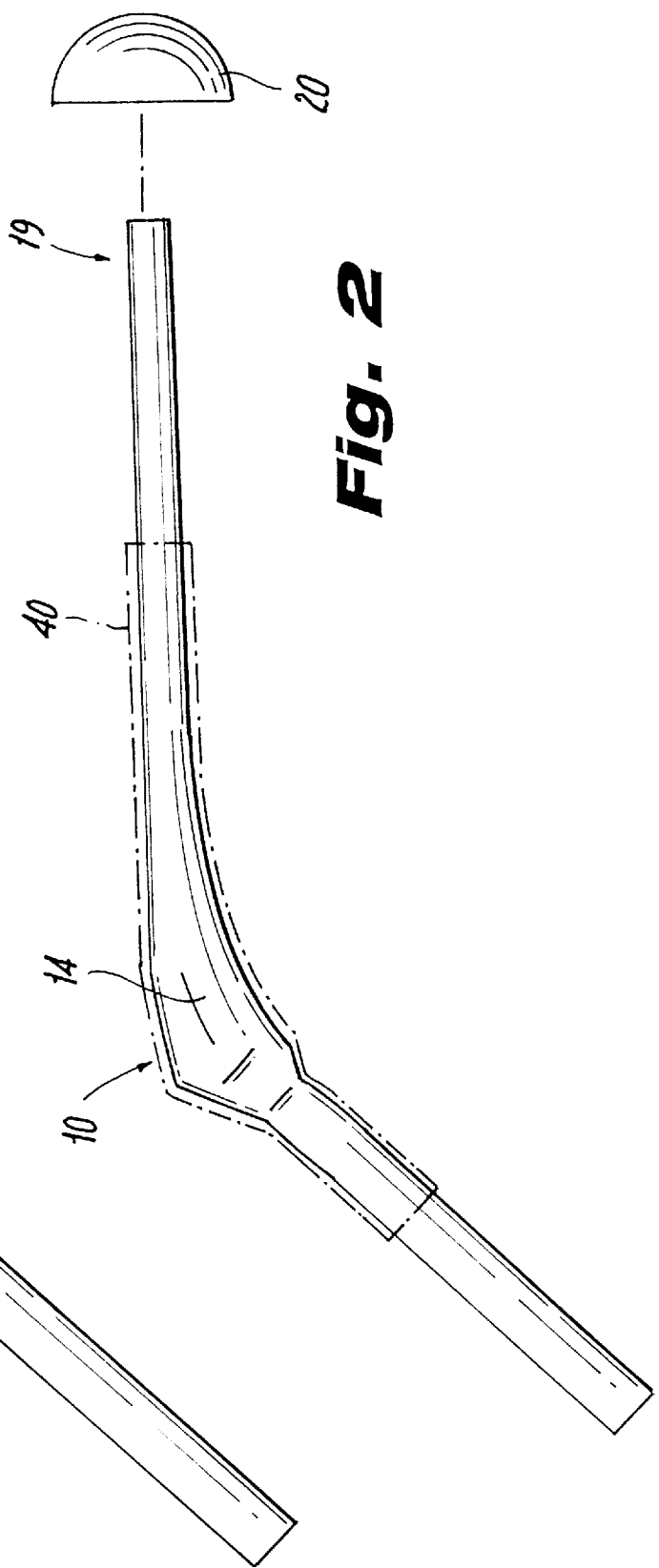

ANTIMICROBIAL ORTHOPEDIC IMPLANTS

FIELD OF THE INVENTION

The invention relates to appliances and devices that are implanted into the body, such as for orthopedic purposes, and that have antimicrobial properties.

BACKGROUND OF THE INVENTION

Various devices are often implanted into the body of a human or animal for orthopedic purposes such as to strengthen bones, as described in U.S. Pat. No. 5,443,513; fasten portions of a bone to correct a fracture, such as in U.S. Pat. No. 4,632,101; and replace joints such as a hip replacement, such as in U.S. Pat. No. 5,522,904. Other joint replacement applications include the knee and small joints such as the fingers.

Such implants can be of metal, of plastic and of composites, such as carbon fibers in a plastic matrix. The outer exposed surfaces of devices implanted into the body come into contact with body tissue and fluids. Since they are foreign in nature to the body they pose a site for growth of bacteria and potential infection. Therefore, it would be desirable to provide such devices with antimicrobial properties so as to reduce the growth of bacteria and risk of infection or to eliminate these problems.

U.S. Pat. No. 5,756,145 describes the infection problem caused by medical implants, such as a replacement hip joints, and seeks to solve the problem by providing the implant with an antimicrobial coating layer that is covered by one or more protective coating layers. The antimicrobial materials considered are basically of a liquid organic type that require a protective coating layer. This increases the complexity of providing the implant with the desired antimicrobial property. Also, consideration has to be given to the durability of the coating and the effectiveness of the antimicrobial action due to the coating.

BRIEF DESCRIPTION OF THE INVENTION

The present invention relates to devices implantable into the body, such as for orthopaedic purposes, having antimicrobial properties produced by an inorganic antimicrobial agent. In a preferred embodiment of the invention, the agent is a zeolite. In the case of the device being of metal, the agent is incorporated in a coating that is applied to the surface of the device. With the device being of a polymer (plastic) or a composite of fibers and plastic resin, the resin forming the implant includes the agent. In either case the exposed surface of the implant has an inorganic antimicrobial agent that contacts the body tissue or fluids and kills bacteria.

OBJECTS OF THE INVENTION

It is therefore an object of the invention to provide an orthopaedic implant device that includes an inorganic antimicrobial agent.

A further object is to provide an orthopaedic implant having an inorganic zeolite on its surface to provide antimicrobial action.

Yet another object is to provide an orthopaedic implant of polymeric resin material including an inorganic antimicrobial agent.

An additional object is to provide an orthopaedic implant of metal having a coating on its surface that contains an inorganic antimicrobial agent.

BRIEF DESCRIPTION OF THE DRAWINGS

Other objects and advantages of the present invention will become more apparent upon reference to the following specification and annexed drawings in which:

FIG. 1 is an elevational view of a typical orthopaedic device that is surgically implanted in the body; and FIG. 2 is a view of the same device with the agent contained in a coating on the device surface.

DETAILED DESCRIPTION OF THE INVENTION

FIG. 1 shows one type of a typical hip stem surgical orthopaedic implant device 10 of the type used for hip repair of a human. The implant is described in detail in U.S. Pat. No. 5,443,513, which is hereby incorporated by reference. The implant described is for illustrative purposes and the present invention is applicable to all types and sizes of implants.

The hip implant 10 includes the stem, or core, 14 of the desired shape. The aforesaid patent describes the stem 14 as illustratively made of a plastic resin material, i.e. short carbon fiber reinforced thermoplastic, such as polyetheretherketone (PEEK). Implant devices of the desired size and shape can be formed completely of any suitable plastic resin material. The hip stem 14 also can be made of metal, as described below.

One end 19 of the stem is to fit into a cup 20 in a pivotable manner. As is conventional, the cup 20 is usually a composite of a resin core, such as ultra high molecular weight polyethylene (UHMWPE) or polyethylene, with the core enclosed in a metal shell such as of Ti—6Al—4V. The stem and cup are implanted into the appropriate body parts by the usual surgical techniques.

In accordance with the invention the surfaces of the implant 10 that are to be exposed to body tissue and fluids contains an inorganic antimicrobial agent. In a preferred embodiment where the stem 14 is of resin, the inorganic antimicrobial agent is incorporated into the resin used to make the stem. The agent does not have to be incorporated into the resin for the cup core since this is not exposed, i.e., it is covered by a metal shell. If the implant, such as the stem 14, is of metal, then its surface is coated with a material containing the inorganic agent.

In a typical process for forming the material used to make the devices, a zeolite is used as the antimicrobial agent. Zeolites are often obtained in master batches of pellets of low density polyethylene, polypropylene, UHMWPE or polystyrene, containing 20 wt. % of the zeolite particles. Thus, the pellets of resin containing the zeolite particles can be easily mixed with the resins used as thermoplastic materials used to make the devices or used in antimicrobial coatings to be applied to devices.

As to implant components of resin, suitable zeolites and methods for incorporating them into the resin are disclosed in U.S. Pat. Nos. 4,938,955 and 4,906,464. The resins can be those such as polyethylene, polypropylene, polystyrene, polyvinyl chloride, ABS resins, silicones, and mixtures thereof, and others disclosed in said patents. An UHMWPE is preferred for the implant devices.

For example in making a resin device, such as cup or tibial plateau, the resin pellets containing the zeolite particles are kneaded into the resin for the device. The pellets can be ground to any desired size. Both of these can be, for example, of UHMWPE. The composite of the implant resin and the resin zeolite pellets is then processed in a conventional manner, such as by injection molding, to form the plastic core for the cup 20 described above or any other device, such as the stem 14 itself. The particles of the agent will be at the exposed surface of the device as formed to be contacted by the body tissue and fluid. Other antimicrobial agents, as described below, are also suitable and would be processed in a manner consistent with the agent and resin used.

The antimicrobial resin particles are preferably present in a concentration by weight in the resin used to make the implant in an effective amount. This means that there is a sufficient amount of the antimicrobial agent added to or combined with other materials, such as the plastic resin, so as to prevent or inhibit the growth of bacterial and/or fungal organisms or to kill such organisms. The amount of the agent will vary based on the specific agent used and the material with which it is mixed or added to and upon known factors such as type and use of the device. Environmental factors such as body temperature also should be taken into consideration. In view of this disclosure, it is within the ability of one skilled in the art to relatively easily determine an effective amount of the antimicrobial agent to be used with each material.

Typical ranges of the zeolite agent particles in the composite resin for the device have been found to be of from 0.01 to 10.0 wt %, more preferably from 0.01 to 8.0 wt %, and most preferably from 0.1 to 5.0 wt %.

In one embodiment of the device of U.S. Pat. No. 5,443,513, the core 14 is helically wound with layers of elongated filament fibers embedded in a thermoplastic polymer resin, sometimes called a prepreg. In accordance with the present invention the agent would be mixed with the thermoplastic polymer resin in the manner described above and be present on the outer surface of the tape which comes into contact with the body tissue, thereby providing the basis for the antimicrobial action.

Configurations suitable for other implants of the general type of FIG. 1 would be made in the same manner. For example, there can be a tibial plateau made of an UHMWPE into which the agent has been incorporated. Here also, the agent would be present at the surface of the device exposed to the body tissue. This would apply to any implant or part that is to be exposed.

FIG. 2 shows the same hip replacement beam type stem 14 and cup 20 as in FIG. 1. Here, the stem is made of a suitable metal, such as such as Ti—6Al—4V, cobalt chrome alloys such as Co—Cr—Mo, stainless steel and nickel-titanium alloys. The metal shell for the cup 20 can be of the same material. The stem 14, and preferably also the cup 20, of this embodiment has a coating 40 containing the antimicrobial agent over a selected area, usually that which will be exposed in the body. The coating can be formed and applied in several different ways.

In one form, the coating is adhered to the metal surface. Polymer coatings are preferred for this embodiment. The polymers can be of silicone rubber and hydrophilic polymers. The coating can be of, for example, a hydrophilic polymer such as hydrophilic polyurethane or a hydrophilic polymer material having a lubricious property, such as shown in U.S. Pat. No. 5,731,087. Particles containing the antimicrobial agent are mixed with the coating material or pellets of the resin coating material. As with the case of the resin, a concentrate of the liquid is made that can be blended with untreated liquid coating material.

The agent particles comprise by weight of the coating material of between about 0.1%–100%, more preferably between about 0.1%–75% and most preferably between about 0.5%–50.0%. As explained above, an effective amount of the agent is added. The coating 40 with the agent is applied to the outer surface of a metal implant, such as the cup 40, by any suitable technique, such as spraying, painting or dipping. The agent is available on the surface of the part to come into contact with the body tissue and perform its antimicrobial action.

The coating with the agent also can be applied to the outer surface of a resin implant.

Powder coating of a metal implant component with the agent also can be used. The powder coating process usually comprises the basic steps of cleaning the metal, electrostatically spraying the powder and baking. Here, the inorganic antimicrobial agent can be incorporated into the powder, either in the original zeolite particle form that is blended with the powder to be sprayed, or the zeolite particles or the pellets of resin containing the zeolite particles may be applied in a second step to the surface of a part already powder coated before the baking step. Incorporation of the inorganic antimicrobial into the powder can be accomplished by preparing a master batch concentrate of the pellets containing the agent particles (same ranges as the concentrate above for the resin) which is then blended into the same or a different polymer used for the spray coating powder to the desired concentration.

The composite of agent containing particles and the spray powder is ground or melt atomized to produce a powder that is used directly or diluted with untreated spray powder used in the conventional powder coating process. The powder is applied in the normal manner.

Again, an effective amount of the agent is used. Typically, this is between 0.1 to 30 wt %, preferably 0.5 to 15 wt %, most preferably 1 to 10 wt % of the final powder sprayed on the device.

An alternate method is to combine untreated polymer powder with a solution of an appropriate solvent, with or without a binder, and add the inorganic antimicrobial particles to coat the inorganic antimicrobial on the polymer powder particles. The solvent is then evaporated and the powder coated with the agent is used in the conventional powder coating process. This ensures that the inorganic antimicrobial is exposed at the surface of the device.

Another method of producing an antimicrobial powder coating is to apply a powder coating onto the device surface in the conventional manner and then apply a coating of the inorganic antimicrobial particles in a solvent or water. The part is then dried and baked as in the conventional powder coating process, thus incorporating the inorganic antimicrobial specifically into the near surface of the coating.

Thus, the antimicrobial zeolites are exceptionally suitable under relevant toxicity and biocompatibility standards for use in the implantable devices.

The preferred antimicrobial agent is an inorganic antimicrobial metal containing composition. A number of metal ions, which are inorganic materials, have been shown to possess antimicrobial activity, including silver, copper, zinc, mercury, tin, lead, bismuth, cadmium, chromium and thallium ions. These antimicrobial metal ions are believed to exert their effects by disrupting respiration and electron transport systems upon absorption into bacterial or fungal cells. Antimicrobial metal ions of silver, gold, copper and zinc, in particular, are considered safe even for in vivo use. Antimicrobial silver ions are particularly useful for in vivo use due to the fact that they are not substantially absorbed into the body. That is, if such materials are used they should pose no hazard.

In one embodiment of the invention, the inorganic antimicrobial metal containing composition is an antimicrobial metal salt. Such salts include silver acetate, silver benzoate, silver carbonate, silver ionate, silver iodide, silver lactate, silver laureate, silver nitrate, silver oxide, silver palpitate, silver protein, and silver sulfadiazine. Silver nitrate is preferred. These salts are particularly quick acting, as no release from ceramic particles is necessary to function antimicrobially.

Antimicrobial zeolites are preferred. These have been prepared by replacing all or part of the ion-exchangeable ions in zeolite with ammonium ions and antimicrobial metal ions, as described in U.S. Pat. Nos. 4,938,958 and 4,911,898. Such zeolites have been incorporated in antimicrobial resins (as shown in U.S. Pat. Nos. 4,938,955 and 4,906,464) and polymer articles (U.S. Pat. No. 4,775,585). Polymers including the antimicrobial zeolites have been used to make refrigerators, dish washers, rice cookers, plastic film, chopping boards, vacuum bottles, plastic pails, and garbage containers. Other materials in which antimicrobial zeolites have been incorporated include flooring, wall paper, cloth, paint, napkins, plastic automobile parts, catheters, bicycles, pens, toys, sand, and concrete. Examples of such uses are described in U.S. Pat. Nos. 5,714,445; 5,697,203; 5,562,872; 5,180,585; 5,714,430; and 5,102,401.

Antimicrobial ceramic particles useful with the present invention include zeolites, hydroxy apatite, zirconium phosphates or other ion-exchange ceramics. Zeolites are preferred, and are described in the preferred embodiments referred to below. Hydroxy apatite particles containing antimicrobial metals are described, e.g., in U.S. Pat. No. 5,009,898. Zirconium phosphates containing antimicrobial metals are described, e.g., in U.S. Pat. Nos. 5,296,238; 5,441,717; and 5,405,644.

Inorganic particles, such as the oxides of titanium, aluminum, zinc and copper, may be coated with a composition which confers antimicrobial properties, for example, by releasing antimicrobial metal ions such as silver ions, which are described, e.g., in U.S. Pat. No. 5,180,585. Inorganic soluble glass particles containing antimicrobial metal ions, such as silver, are described, e.g., in U.S. Pat. Nos. 5,766,611 and 5,290,544.

Antimicrobial zeolites are well-known and can be prepared for use in the present invention using known methods. These include the antimicrobial zeolites disclosed, for example, in U.S. Pat. Nos. 4,938,958 and 4,911,898.

Either natural zeolites or synthetic zeolites can be used to make the antimicrobial zeolites used in the present invention. "Zeolite" is an aluminosilicate having a three dimensional skeletal structure that is represented by the formula: $XM_{2/n}O$—$Al_2O_3$—$YSiO_2$—$ZH_2O$. M represents an ion-exchangeable ion, generally a monovalent or divalent metal ion, n represents the atomic valency of the (metal) ion, X and Y represent coefficients of metal oxide and silica respectively, and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. The present invention is not restricted to use of these specific zeolites.

The ion-exchange capacities of these zeolites are as follows: A-type zeolite=7 meq/g; X-type zeolite=6.4 meq/g; Y-type zeolite=5 meq/g; T-type zeolite=3.4 meq/g; sodalite= 11.5 meq/g; mordenite=2.6 meq/g; analcite=5 meq/g; clinoptilolite=2.6 meq/g; chabazite=5 meq/g; and erionite= 3.8 meq/g. These ion-exchange capacities are sufficient for the zeolites to undergo ion-exchange with ammonium and antimicrobial metal ions.

The specific surface area of preferred zeolite particles is preferably at least 150 $m^2/g$ (anhydrous zeolite as standard) and the $SiO_2/Al_2O_3$ mol ratio in the zeolite composition is preferably less than 14, more preferably less than 11.

The antimicrobial metal ions used in the antimicrobial zeolites should be retained on the zeolite particles through an ion-exchange reaction. Antimicrobial metal ions which are adsorbed or attached without an ion-exchange reaction exhibit a decreased bactericidal effect and their antimicrobial effect is not long-lasting. Nevertheless, it is advantageous for imparting quick antimicrobial action to maintain a sufficient amount of surface adsorbed metal ion.

During the ion-exchange process, if the concentration of metal ions in the vicinity of the zeolite surface is high, there is a tendency for the antimicrobial metal ions (cations) to be converted into their oxides, hydroxides, basic salts, etc., which deposit in the micro pores or on the surfaces of the zeolite. This deposition may adversely affect the bactericidal properties of the ion-exchanged zeolite.

In an embodiment of the antimicrobial zeolites, a relatively low degree of ion exchange is employed to obtain superior bactericidal properties. It is believed to be required that at least a portion of the zeolite particles retain metal ions having bactericidal properties at ion-exchangeable sites of the zeolite in an amount less than the ion-exchange saturation capacity of the zeolite. In one embodiment, the zeolite employed in the present invention retains antimicrobial metal ions in an amount up to 41% of the theoretical ion-exchange capacity of the zeolite. Such ion-exchanged zeolite with a relatively low degree of ion-exchange may be prepared by performing ion-exchange using a metal ion solution having a low concentration as compared with solutions conventionally used for ion exchange.

The antimicrobial metal ion is preferably present in the range of from about 0.1 to 20 wt. % of the zeolite. In one embodiment, the zeolite contain from 0.1 to 20 wt. % of silver ions and from 0.1 to 20 wt. % of copper or zinc ions. Although ammonium ion can be contained in the zeolite at a concentration of about 20 wt. % or less of the zeolite, it is desirable to limit the content of ammonium ions to from 0.5 to 15 wt. %, preferably 1.5 to 5 wt. %. Weight % described herein is determined for materials dried at temperatures such as 110° C., 250° C. or 550° C. as this is the temperature employed for the preferred post-manufacturing drying process.

A preferred antimicrobial zeolite is type A zeolite containing either a combination of ion-exchanged silver, zinc, and ammonium or silver and ammonium. One such zeolite is manufactured by Shinagawa, Inc. under the product number AW-10N and consists of 0.6% by weight of silver ion-exchanged in Type A zeolite particles having a diameter of about 2.5μ. Another formulation, AJ-10N, consists of about 2% by weight silver ion-exchanged in Type A zeolite particles having a diameter of about 2.5μ. Another formulation, AW-80, contains 0.6% by weight of silver ion-exchanged in Type A zeolite particles having a diameter of about 1.0μ. Another formulation, AJ-80N, consists of about 2% by weight silver ion-exchanged in Type A zeolite particles having a diameter of about 1.0μ. These zeolites preferably contain about between 0.5% and 2.5% by weight of ion-exchanged ammonium. Type AJ10D consists of about 2.5% by weight of silver ion-exchanged in Type A zeolite particles having a diameter of about 1.0μ.

The zeolites are often obtained in master batches of low density polyethylene, polypropylene, or polystyrene, containing 20 wt. % of the zeolite. Thus, they can be easily mixed with the resins used as materials for forming a composite resin used to make the device.

The antimicrobial properties of the antimicrobial zeolite particles of the invention may be assayed while in aqueous formulations using conventional assay techniques, including for example determining the minimum growth inhibitory concentration (MIC) with respect to a variety of bacteria, eumycetes and yeast. In such a test, the bacteria listed below may be employed:

*Bacillus cereus varmycoides;*
*Escherichia coli;*
*Pseudomonas aeruginosa;*
*Staphylococcus aureus;*
*Streptococcus faecalis;*
*Aspergillus niger;*
*Aureobasiduim pullulans;*
*Chaetomium globosum;*
*Gliocladium virens;*
*Penicillum funiculosum;*
*Candida albicans; and*
*Saccharomyces cerevisiae.*

The assay for determining MIC can be carried out by smearing a solution containing bacteria for inoculation onto a plate culture medium to which a test sample of the encapsulated antimicrobial zeolite particles is added in a particular concentration, followed by incubation and culturing of the plate. The MIC is defined as a minimum concentration thereof required for inhibiting the growth of each bacteria.

Safety and biocompatibility tests were conducted on the antimicrobial zeolites employed in the invention. ISO 10993-1 procedures were employed. The following results were obtained:

| |
|---|
| Cytotoxicity: Non-Toxic |
| Acute Systemic Toxicity: Non-Toxic |
| Oral Toxicity: Safer than table salt |
| Intracutaneous Toxicity: Passed |
| Skin Irritation Test: Non-Irritant |
| Chronic Toxicity: No Observable Effect |
| In-vitro Hemolysis: Non-Hemolytic |
| 30-day Muscle Implant Test: Passed |
| 60-day Muscle Implant Test: Passed |
| 90-day Muscle Implant Test: Passed |
| Ames Mutagenicity Test: Passed |
| Pyrogenicity: Non-Pyrogenic |

Thus, the antimicrobial zeolites are exceptionally suitable under relevant toxicity and biocompatibility standards for use in the implantable devices.

An embodiment of the orthopedic implant formed from a resin has the following components:

| | |
|---|---|
| plastic resin of device | UHMWPE |
| material of agent | silver zeolite (preferably type AJ10D) |
| wt. % of agent in composite | 5.0% |
| size of the agent particles | 1.0 micron |

A typical embodiment of the metal orthopedic implant that is coated is

| | |
|---|---|
| metal of device | Ti-6A1-4V |
| material of agent | silver zeolite (preferably type AJ10N) |
| coating material | urethane |
| wt. % of agent in coating | 30.0% of coating |
| size of the agent particles | 1.0 micron |

A typical embodiment of the powder coated orthopedic implant is

| | |
|---|---|
| metal of device | Ti-6A1-4V |
| material of agent | silver zeolite (preferably type AJ10N) |
| powder coating material | silica |
| wt. % of agent in powder | 10.0% |
| size of the agent particles | 1.0 micron |

Specific features of the invention are shown in one or more of the drawings for convenience only, as each feature may be combined with other features in accordance with the invention. Alternative embodiments will be recognized by those skilled in the art and are intended to be included within the scope of the claims.

While preferred embodiments of the invention have been described in the foregoing examples, it will be understood by one skilled in the art that various changes and modifications may be made therein without departing from the spirit and the scope of the invention. All patent applications, patents, patent publications, and literature references cited in this specification are hereby incorporated by reference in their entirety. In the case of inconsistencies, the present description, including definitions, is intended to control. Accordingly, the above description should be construed as illustrating and not limiting the scope of the invention. All such obvious changes and modifications are within the patented scope of the appended claims.

We claim:
1. An orthopedic surgical implant comprising:
   (a) at least one component having a surface which contacts body tissue or fluid when implanted and
   (b) antimicrobial ceramic particles comprising ion-exchanged antimicrobial metal cations present at a level less than the ion-exchange capacity of the ceramic particles
   wherein the antimicrobial ceramic particles are present at said surface and are capable of releasing the antimicrobial metal cations in an antimicrobially effective amount.
2. The orthopedic surgical implant of claim 1 wherein said at least one component is of metal.
3. The orthopedic surgical implant of claim 1 wherein the antimicrobial metal cations are silver cations.
4. The orthopedic surgical implant of claim 1 wherein the antimicrobial ceramic particles are selected from the group consisting of zeolites, hydroxy apatite and zirconium phosphates.
5. The orthopedic surgical implant of claim 1 wherein the antimicrobial metal ions are selected from the group consisting of gold, silver, copper and zinc ions.
6. The orthopedic surgical implant of claim 1 wherein said at least one component comprises metal and said surface comprises a coating adhered to said at least one component and containing said antimicrobial ceramic particles.
7. The orthopedic surgical implant of claim 1 wherein said at least one component comprises a plastic resin containing said antimicrobial ion-exchange ceramic particles.

8. The orthopedic implant of claim 1 having first and second components, said first component comprising a plastic resin incorporating said antimicrobial zeolite particles.

9. The orthopedic implant of claim 1 having first and second components, said first component comprising a plastic resin incorporating said antimicrobial zeolite particles and said second component having a coating applied thereto that contains said antimicrobial zeolite particles.

10. The orthopedic implant of claim 9 wherein the second component comprises metal.

11. The orthopedic implant of claim 7 wherein the plastic resin is ultra high molecular weight polyethylene.

12. The orthopedic implant of claim 7 wherein the antimicrobial ceramic particles comprise from 0.25% to 10% by weight of the plastic resin.

13. The orthopedic implant of claim 1 wherein the antimicrobial metal cation is present at a level below the ion-exchange capacity in at least a portion of the antimicrobial ceramic particles.

14. The orthopedic implant of claim 1 wherein the antimicrobial metal cation is present at a level below the ion-exchange capacity in at least a portion of the antimicrobial zeolite particles.

15. An orthopedic surgical implant comprising:
(a) at least one component having a surface which contacts body tissue or fluid when implanted and
(b) antimicrobial zeolite particles comprising ion-exchanged antimicrobial metal cations present at a level less than the ion-exchange capacity of the zeolite wherein the antimicrobial zeolite particles are present at said surface and are capable of releasing the antimicrobial metal cations in an antimicrobially effective amount.

16. The orthopedic surgical implant of claim 15 wherein the antimicrobial metal cations are silver cations.

17. The orthopedic implant of claim 15 wherein said at least one component comprises a plastic resin containing said antimicrobial zeolite particles.

18. The orthopedic surgical implant of claim 17 wherein said plastic resin is ultra high molecular weight polyethylene.

19. The orthopedic surgical implant of claim 17 wherein said antimicrobial zeolite particles comprise from 0.25% to 10.0% by total weight of said plastic resin.

20. The orthopedic implant of claim 15 wherein said at least one component comprises metal.

21. The orthopedic implant of claim 15 having first and second components, said first component comprising a plastic resin incorporating said antimicrobial zeolite particles, and said second component having a coating applied thereto that contains said antimicrobial zeolite particles.

22. The orthopedic surgical implant of claim 21 wherein said second component comprises a metal to which said coating is adhered.

23. The orthopedic surgical implant of claim 15 wherein the size of said antimicrobial zeolite particles is from 0.25 to 10.0 microns.

24. The orthopedic surgical implant of claim 15 wherein said at least one component comprises metal and said surface comprises a coating adhered to said at least one component and containing said antimicrobial zeolite particles.

25. The orthopedic surgical implant of claim 15 wherein the antimicrobial metal ions are selected from the group consisting of gold, silver, copper and zinc ions.

* * * * *